(12) United States Patent
Chen (10) Patent No.: US 7,794,433 B2
(45) Date of Patent: Sep. 14, 2010

(54) ASSEMBLY OF PLUNGER AND NEEDLE HUB SAFETY SYRINGE NEEDLE DEVICE

(76) Inventor: Cho-Ying Chen, No. 193, Dajhou Rd., Shengang Township, Taichung County 429 (TW)

(*) Notice: Subject to any disclaimer, the term of this patent is extended or adjusted under 35 U.S.C. 154(b) by 368 days.

(21) Appl. No.: 11/700,161

(22) Filed: Jan. 31, 2007

(65) Prior Publication Data

US 2007/0244443 A1    Oct. 18, 2007

(30) Foreign Application Priority Data

Mar. 22, 2006   (TW) ............................... 95204787 U (51) Int. Cl.
*A61M 5/32* (2006.01)
(52) U.S. Cl. ..................................................... 604/195
(58) Field of Classification Search ................. 604/195, 604/110, 187
See application file for complete search history.

(56) References Cited

U.S. PATENT DOCUMENTS 5,554,129 A * 9/1996 Stevenson .................... 604/192
6,391,008 B1 * 5/2002 Tsai ............................ 604/195
6,976,976 B2 * 12/2005 Doyle .......................... 604/198

* cited by examiner

Primary Examiner—Nicholas D Lucchesi
Assistant Examiner—Brooke M Matney
(74) Attorney, Agent, or Firm—Wang Law Firm; Li K. Wang (57) ABSTRACT

An improved assembly of plunger and needle hub for a safety syringe needle device is disclosed, which comprises a syringe barrel, a needle hub and a plunger. The syringe barrel is shaped as a tube and has an interior periphery thereof shaped as a straight tube. The needle hub is inserted into the syringe barrel and has an integrated combining ring, which is bent inward as a hook and has a crease whereon the combining ring is bent inward. The needle hub has a nozzle jutting out of the syringe barrel for connecting a needle. The plunger comprises a plug for being fitly received by the syringe barrel and a front end thereof can be pierced through and coupled with the combining ring.

4 Claims, 9 Drawing Sheets

ASSEMBLY OF PLUNGER AND NEEDLE HUB SAFETY SYRINGE NEEDLE DEVICE

BACKGROUND OF THE INVENTION

1. Technical Field

The present invention relates to an improved assembly of plunger and needle hub for a safety syringe needle device and, more particularly, to a safety syringe needle device with a retractable needle hub that has integrated combining ring formed as inward-bent hooks for being engaged with a plunger and capable of being retracted back to the syringe accompanying retreat of the plunger.

2. Description of Related Art

Figure 8:
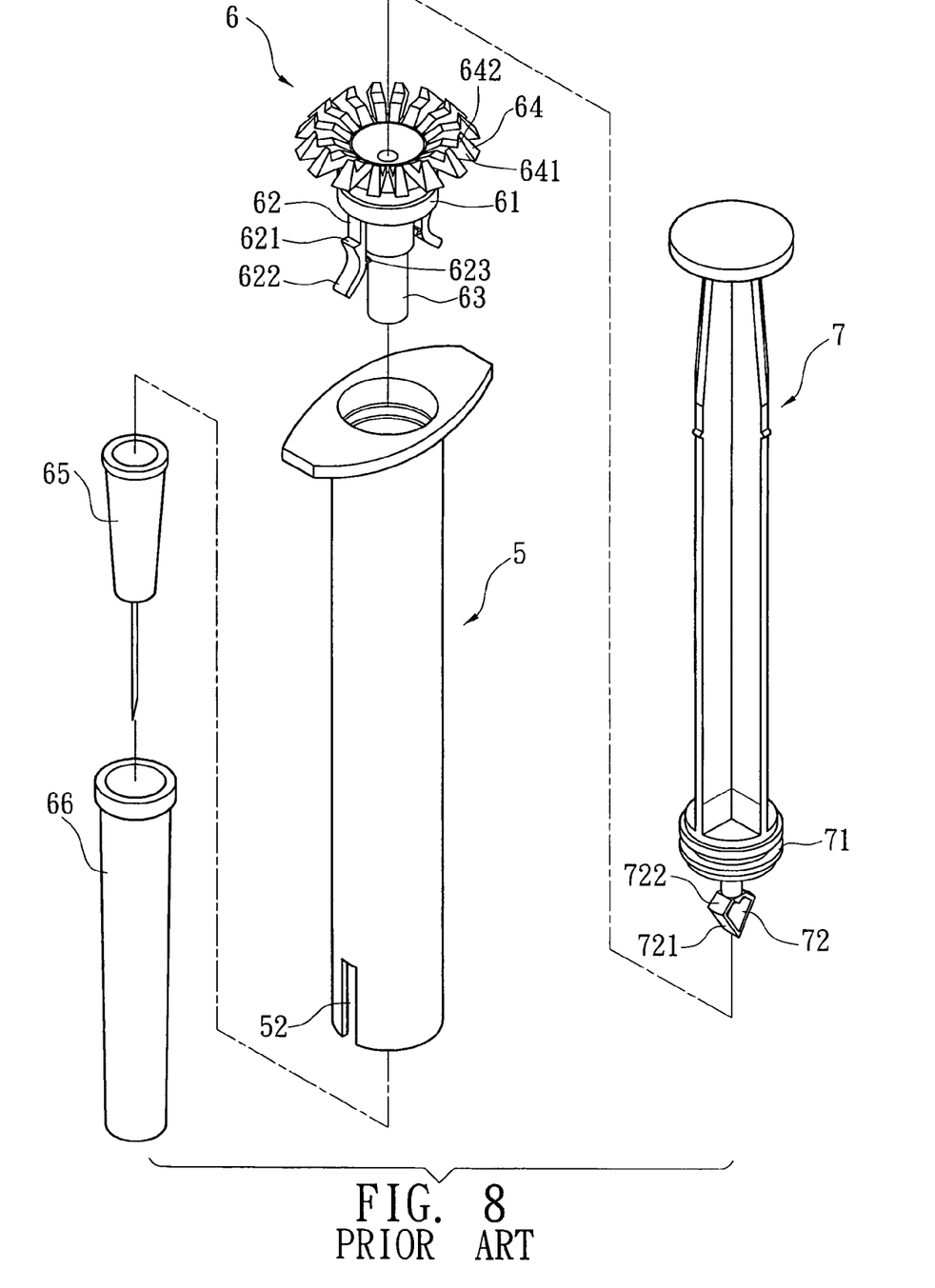
FIG. 8 is an exploded view of a conventional assembly of plunger and needle hub for a safety syringe needle device.
Figure 9:
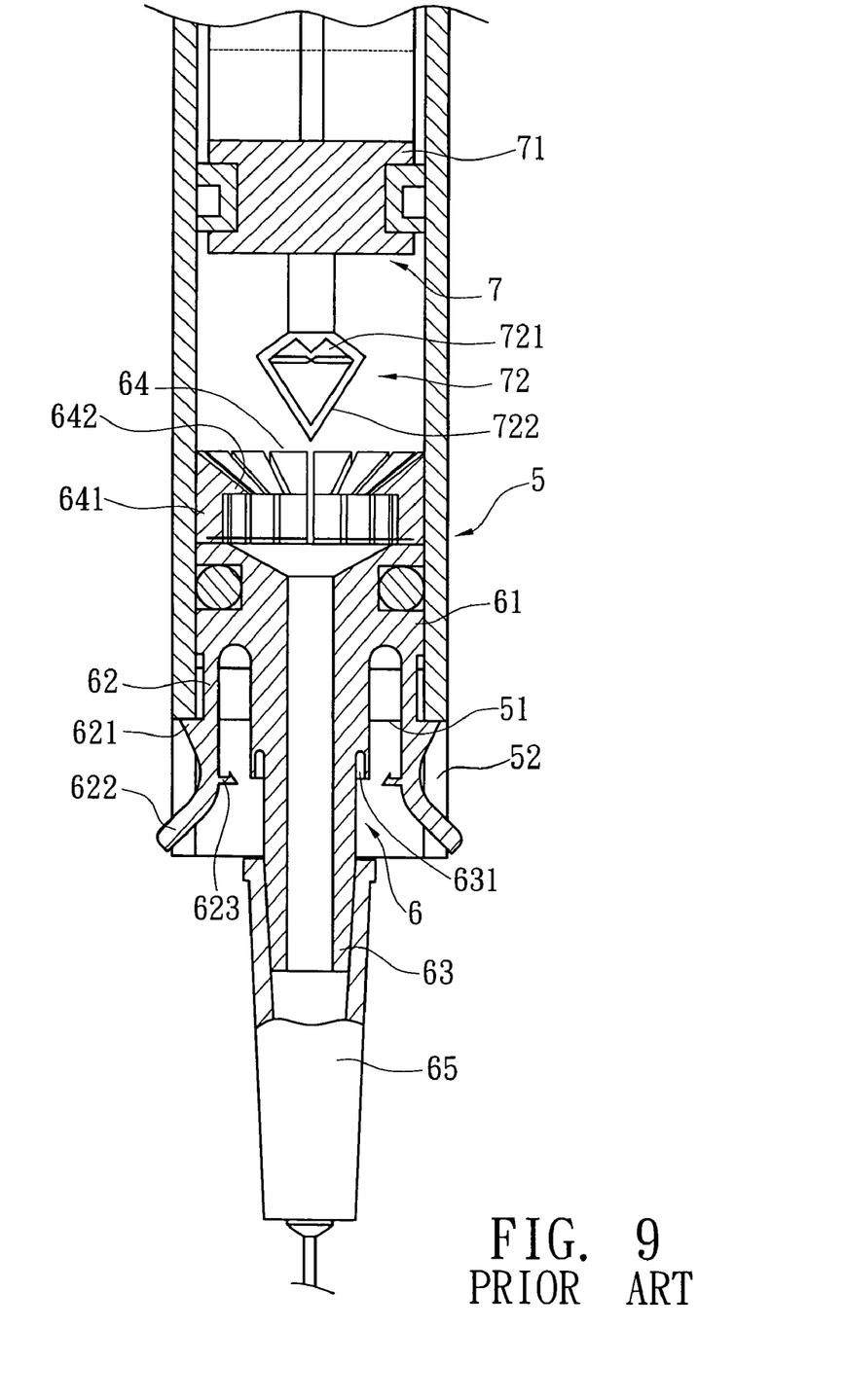
FIG. 9 is a schematic cross-sectional view of the conventional assembly of plunger and needle hub for a safety syringe needle device.

A conventional safety syringe needle device is illustrated through FIGS. 8 and 9, which is primarily composed of a tubular syringe barrel 5, a needle hub 6 and a plunger 7, wherein the interior periphery of the syringe barrel 5 is shaped as a straight tube, and inside the syringe barrel 5, a flange 51 is provided adjacent to the front end thereof while two opposite notches 52 are arranged at the front end of the syringe barrel 5.

Said needle hub 6 is inserted into the syringe barrel 5 and has a retaining ring 61, which comprises a plurality of retaining hooks 62, each having a hook portion 621 for being engaged with the notches 52 of the syringe barrel 5 and a snap segment 622 settled at the outer edge thereof. As there is an interval between the retaining hooks 62 and the retaining ring 61, the syringe barrel 5 can hold the needle hood 6 by implementing the flange 51 to retain the retaining ring 61 and press upon the retaining hooks 62. Moreover, the retaining ring 61 further comprises a nozzle 63, which is jutting out of the syringe barrel 5 and comprises a recess 631 positioned corresponding to the retaining hooks 62. In the meantime, each of the retaining hooks 62 has a combining portion 623 positioned corresponding to the recess 631 so that when the combining portions 623 is engaged with the recess 631, the retaining hooks 62 can be squeezed and the hook portions 621 can be withdrawn from engaging the syringe barrel 5. Furthermore, a combining portion 64 is extended from the needle hub 6 and is composed of a plurality of flexible pieces 641 each having a retaining portion 642. Also, a needle 65 and a sheath 66 can be sleeved onto the nozzle 63.

The plunger 7 comprises a plug 71 for being fitly received by the syringe barrel 5. The plug 71 further has a combining portion 72 protruding at the front end thereof wherein the combining portion 72 includes two wings 721 each attached by an extended retaining piece 722 and the combining portion 72 is thereby formed as a diamond-shaped structure. Thus, the combining portion 72 and the combining portion 64 can be assembled by piercing the combining portion 72 through the combining portion 64 to make the retaining pieces 722 retained by the retaining portions 642 of the combining portion 64.

Accordingly, as the plural pieces 641 of the combining portion 64 of the needle hub 6 are quite complicated in the structure, the components need to be made very precisely in order to ensure appropriate combination with the combining portion 72 and the manufacturing cost can be consequently raised.

Hence, a need exists for an improvement on the conventional assembly of plunger and needle hub for a safety syringe needle device.

SUMMARY OF THE INVENTION

The present invention has been accomplished under these circumstances in view. It is one objective of the present invention to provide an improved assembly of plunger and needle hub for a safety syringe needle device with a retractable needle hub that has an integrated combining ring formed as inward-bent hooks for being engaged with a plunger and capable of being retracted back to the syringe accompanying retreat of the plunger. The disclosed assembly facilitates safe and convenient use. Additionally, because of the relatively uncomplicated structure of the integrated needle hub and combining ring, the manufacturing cost of the disclosed assembly can be significantly reduced.

To achieve these and other objectives of the present invention, the improved assembly of plunger and needle hub for a safety syringe needle device comprises:

a tubular syringe barrel, which is shaped as a tube and has an interior periphery thereof shaped as a straight tube wherein two opposite ends of the syringe barrel are respectively defined as a front end and a rear end;

a needle hub, which is inserted into the syringe barrel and comprises a retaining ring, which is sleeved by a packing ring at the external edge thereof, an accommodating room formed at one end thereof and a an axially tapered combining ring wherein, a crease is formed between the interior periphery of the combining ring and the accommodating room is defined between the retaining ring and the combining ring, wherein the retaining ring can be bent inward to the accommodating room, and the needle hub further comprises a nozzle, which is jutting out from the syringe barrel and for being mounted by a needle; and a plunger, which comprises a plug for being fitly received by the syringe barrel wherein the plug further has a packing ring sleeved around the edge thereof and the front end of the plug can be coupled with the combining ring of the needle hub.

BRIEF DESCRIPTION OF THE DRAWINGS

The invention as well as a preferred mode of use, further objectives and advantages thereof, will best be understood by reference to the following detailed description of an illustrative embodiment when read in conjunction with the accompanying drawings, wherein.

DETAILED DESCRIPTION OF THE PREFERRED EMBODIMENT

Please refer to FIGS. 1 to 6, which describe a preferred embodiment of the present invention. It is to be understood that the recited figures and embodiment are for illustrating and not intended to limit the structure of the present invention.

According to one embodiment of the present invention, a safety syringe needle device may comprise some components, which are explained in more detail below.

Figure 1:
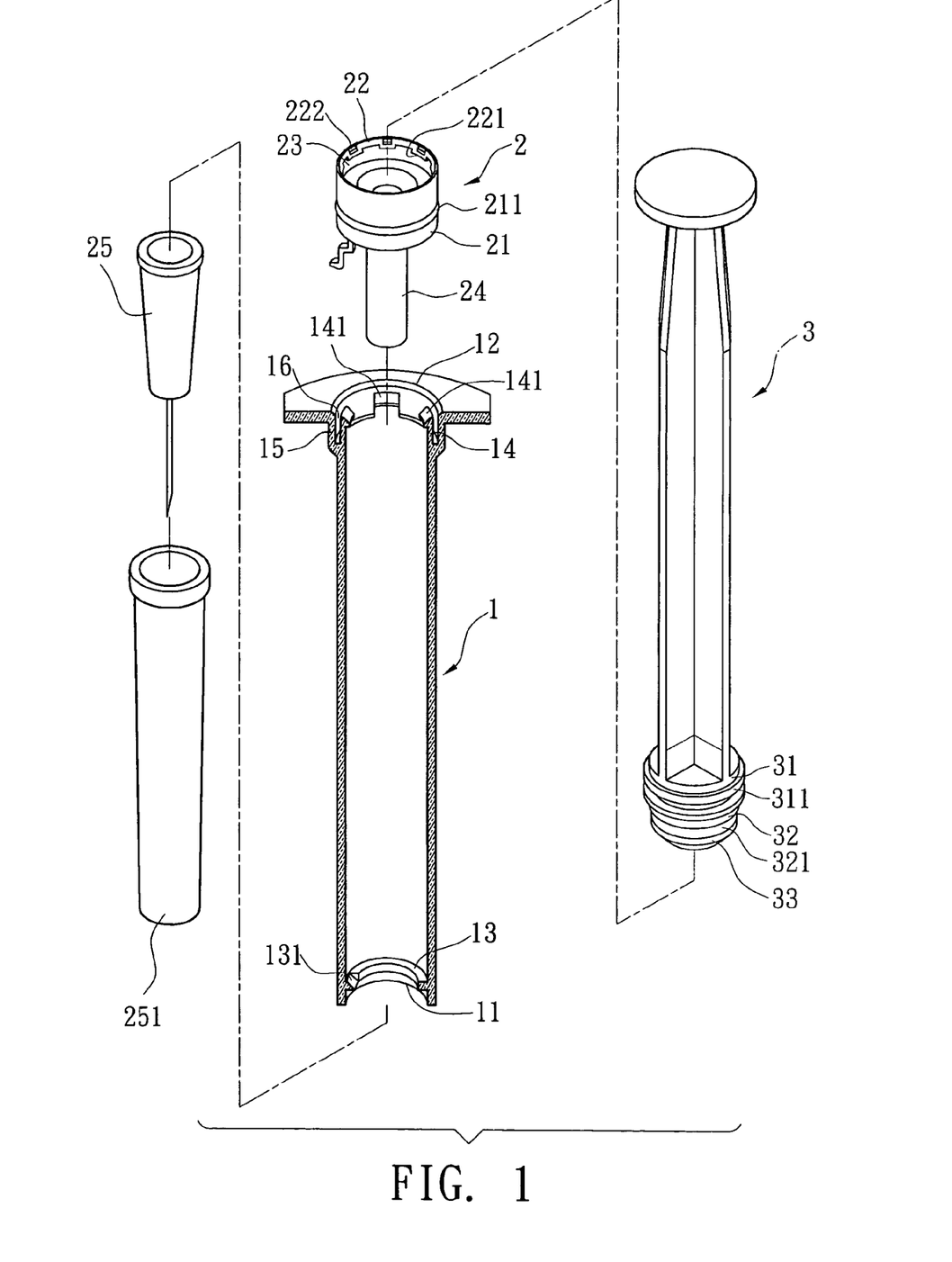
FIG. 1 is an exploded view of a first embodiment of the present invention.
Figure 2:
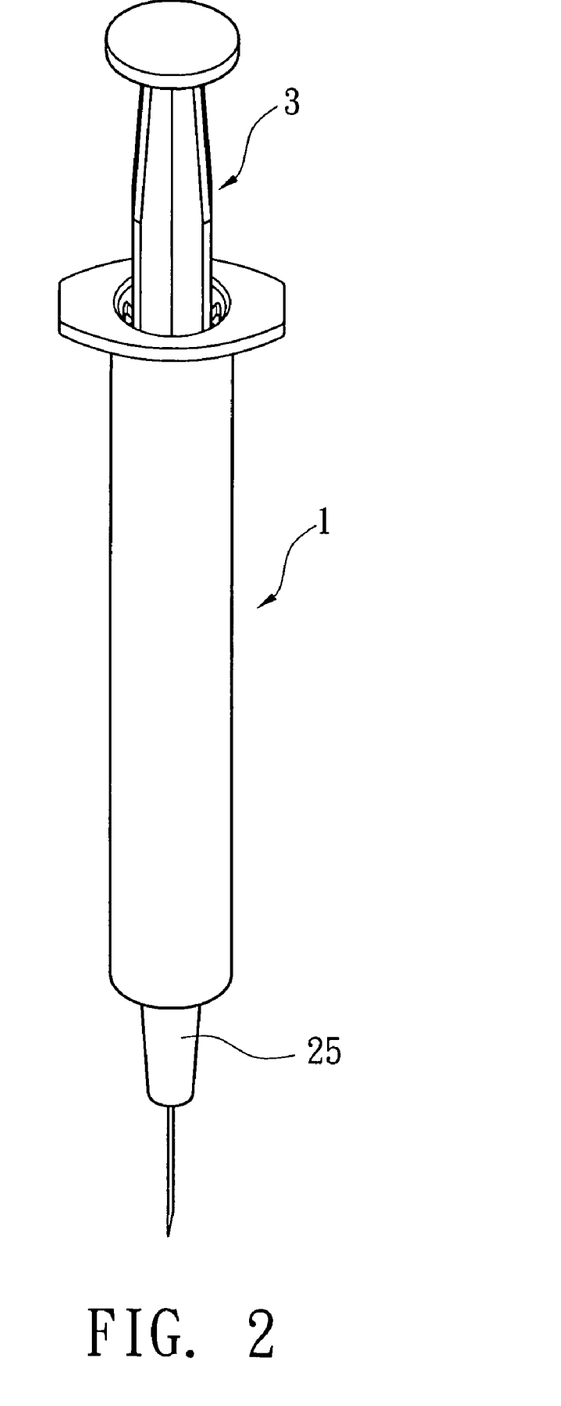
FIG. 2 is a perspective view of the first embodiment of the present invention.
Figure 4:
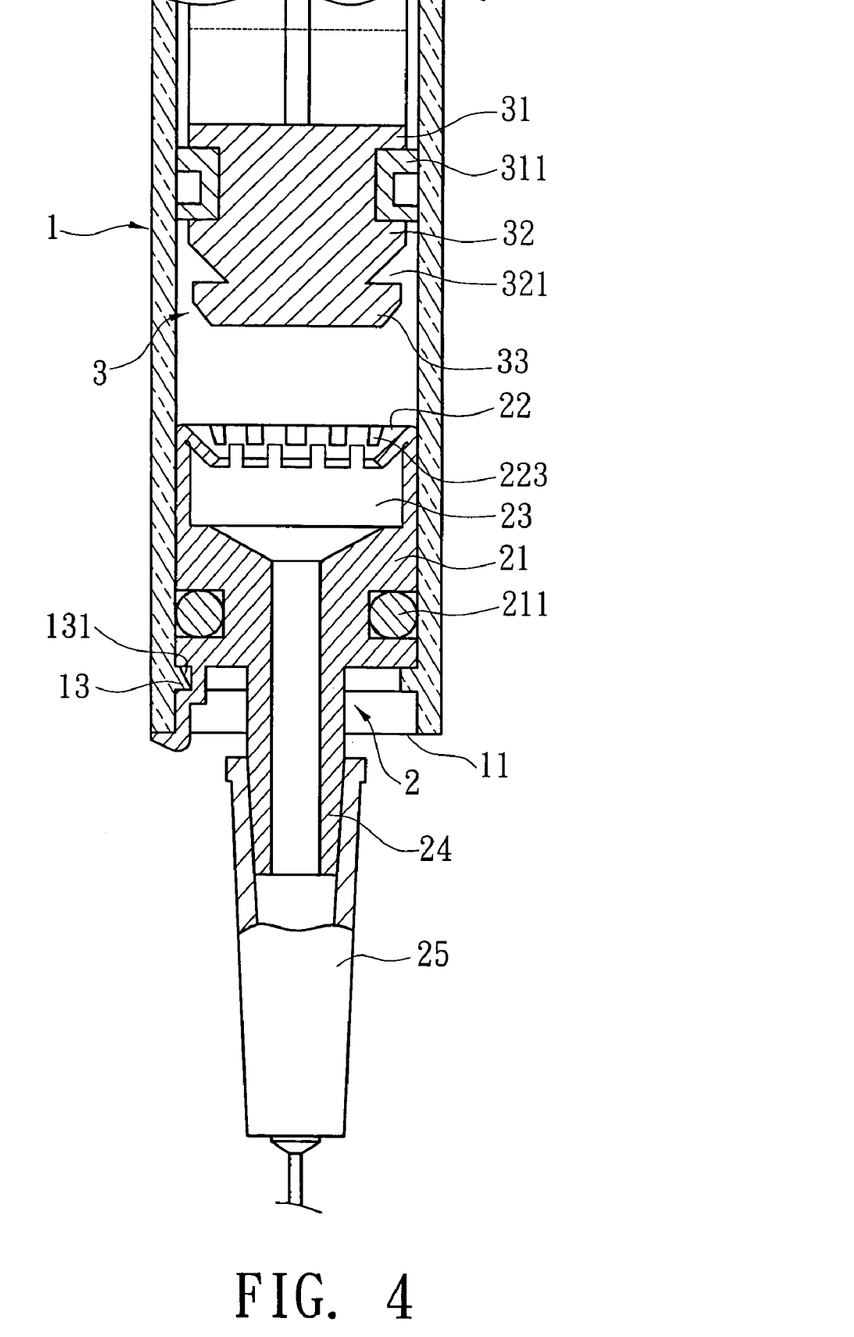
FIG. 4 is a schematic cross-sectional view of the first embodiment of the present invention.

A tubular syringe barrel 1, which is shaped as a tube and has an interior periphery thereof shaped as a straight tube wherein two opposite ends of the syringe barrel 1 are respectively defined as a front end 11 and a rear end 12. Further, a flange 13 is settled at the interior periphery of the syringe barrel 1 adjacent to the front end 11 thereof, and the flange 13 has an incline cut 131 thereon. A retaining portion 14 is provided at the interior periphery at the rear end 12 of the syringe barrel 1. According to the present embodiment, the retaining portion 14 is substantially composed of four inward-bent hooks 141, which are equally spaced. A peripherally enlarged annular segment 15 is extended from the rear end 12 of the syringe barrel 1 and is separated from the outer side of the inward-bent hooks 141 with an interval 16.

Figure 3:
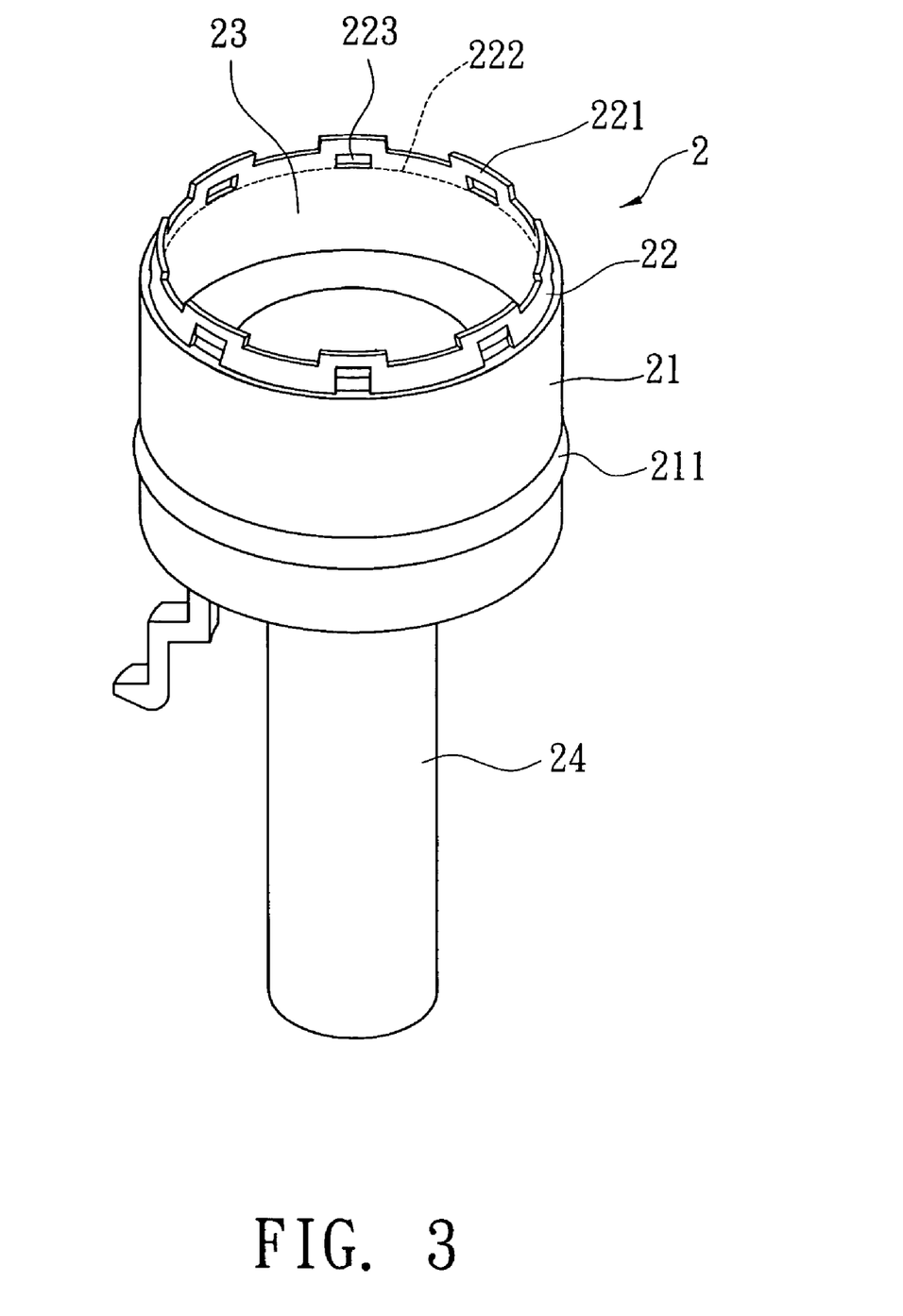
FIG. 3 is a perspective view of the needle hub with the retaining ring not yet bent according to the first embodiment of the present invention.

A needle hub 2 is inserted into the rear end 11 of the syringe barrel 1 and is retained by the flange 13. The needle hub 2 comprises a retaining ring 21, which is sleeved by a packing ring 211 at the external edge thereof and has an accommodating room 23 formed at one end thereof. Also, the retaining ring 21 comprises an integrally extended and axially tapered combining ring 22, which comprises a plurality of teeth 221 protruding at the upper edge of the combining ring 22. Furthermore, a crease 222 is formed between the interior periphery of the combining ring 22 and the retaining ring 21, and a through hole 223 is settled at the lower edge of each of the said teeth 221 and comes into close proximity with the crease 222 to provide further flexibility to the combining ring 22, whereby when the combining ring 22 is bent toward the accommodating room 23, it can be formed into a hook. The opposite end of the retaining ring 21 has a nozzle 24, which is jutting out from the syringe barrel 1 and for being mounted by a needle 25. Further, the needle 25 can be sheathed within a sheath 251.

A plunger 3 comprises a plug 31 for being fitly received by the syringe barrel 1. The plug 31 further has a packing ring 311 sleeved around the edge thereof. For being assembled to the needle hub 2, in the present embodiment, a combining portion 32 is jutting out from the front end of the plug 31, wherein an annular protrusion 33 situated at the front end of the combining portion 32 has a sectional diameter smaller than the diameter of the accommodating room 23 of the needle hub 2 and the combining portion 32 has an acute-angled annular recess 321 formed adjacent to the edge of the annular protrusion 33.

Figure 5:
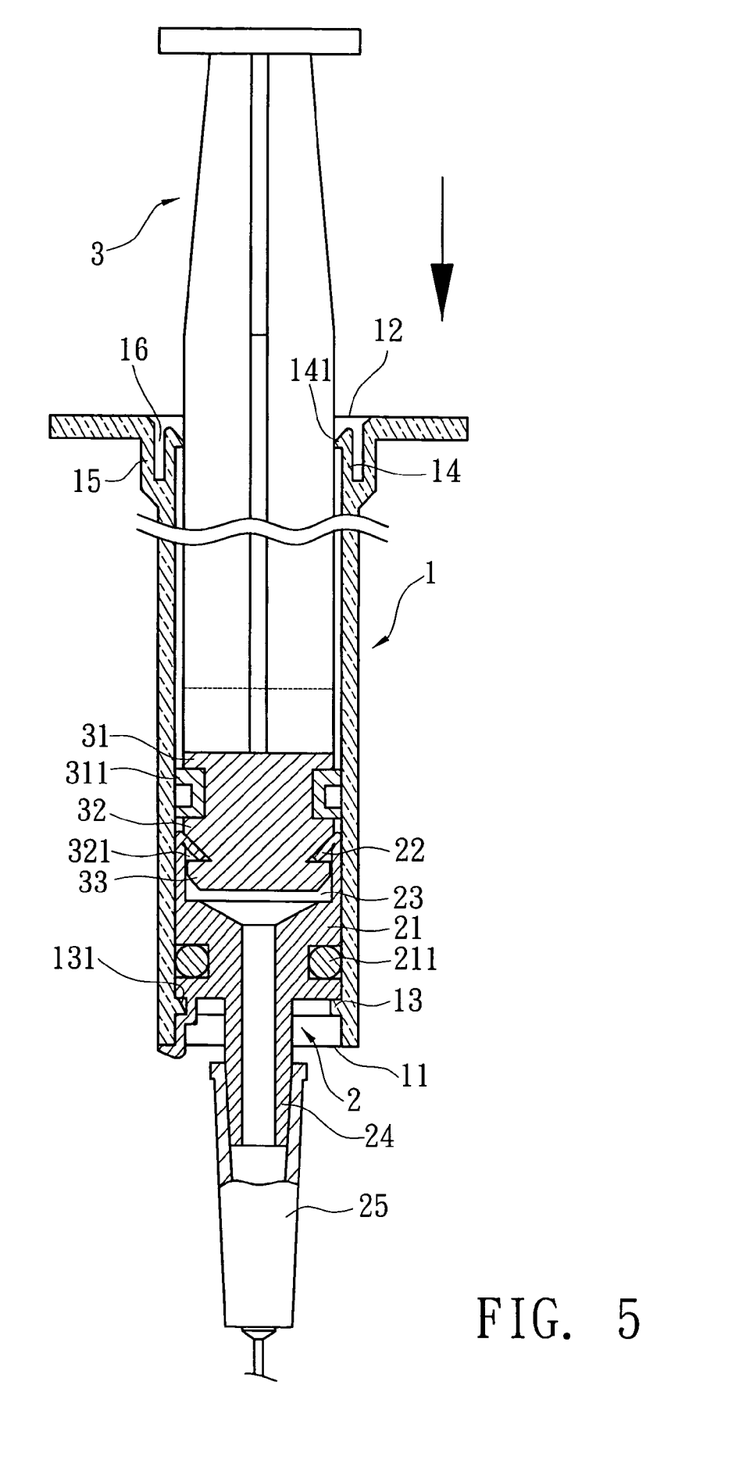
FIG. 5 is one applied view showing the operation of the present invention according to the first embodiment.

Reference is now made to FIG. 5. After using the syringe needle device, when a user pushes the plunger 3 back to the syringe barrel 1, since the diameter of the annular protrusion 33 is larger than the diameter of the extreme of the combining ring 22 of the needle hub 2, the annular protrusion 33 of the plunger 3 has to be shoehorned through the combining ring 22 of the needle hub 2 to enter the accommodating room 23 of the needle hub 2. Afterward, the combining ring 22 of the needle hub 2 can recover and embed itself in the annular recess 321 to couple with the plunger 3.

Figure 6:
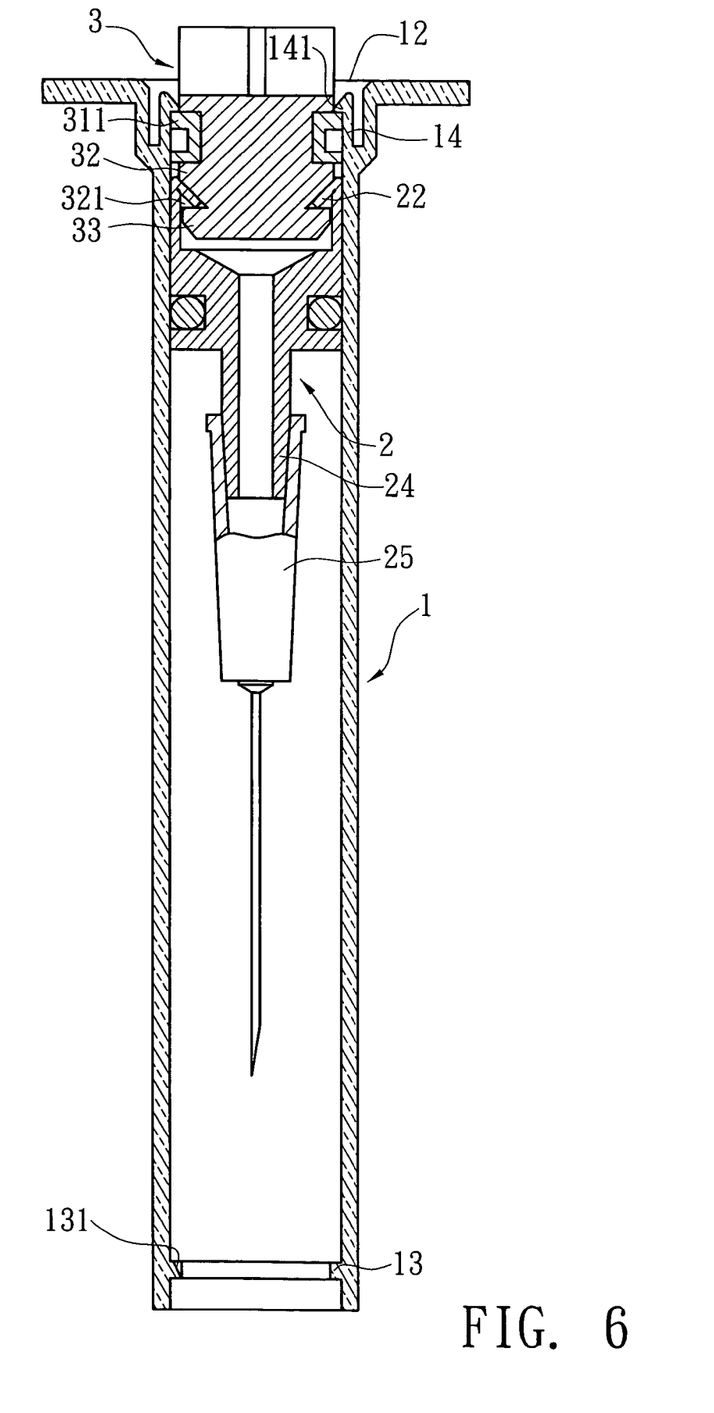
FIG. 6 is another applied view showing the operation of the present invention according to the first embodiment.

As illustrated in FIG. 6, when the plunger 3 is subsequently pulled backward, the needle hub 2 is drawn inward the syringe barrel 1 accordingly. Therefore, the needle hub 2 and needle 25 can be retracted and accommodated in the syringe barrel 1 then. When the plunger 3 is pulled, the inward-bent hooks 141 of the retaining portion 14 retains the needle hub 2 so as to prevent the needle hub 2 and needle 25 from undesirably coming off the syringe barrel 1. After that, the part jutting out from the syringe barrel 1 of the plunger 3 can be trimmed off and the needle hub 2 and needle 25 can be kept in the syringe barrel 1 safely.

Accordingly, the disclosed assembly of plunger and needle hub for a safety syringe needle device is advantageous by not only facilitating safe and convenient use, but also significantly reducing the mold-making cost because of the relatively uncomplicated structure of the needle hub 2 and combining ring 22.

Figure 7:
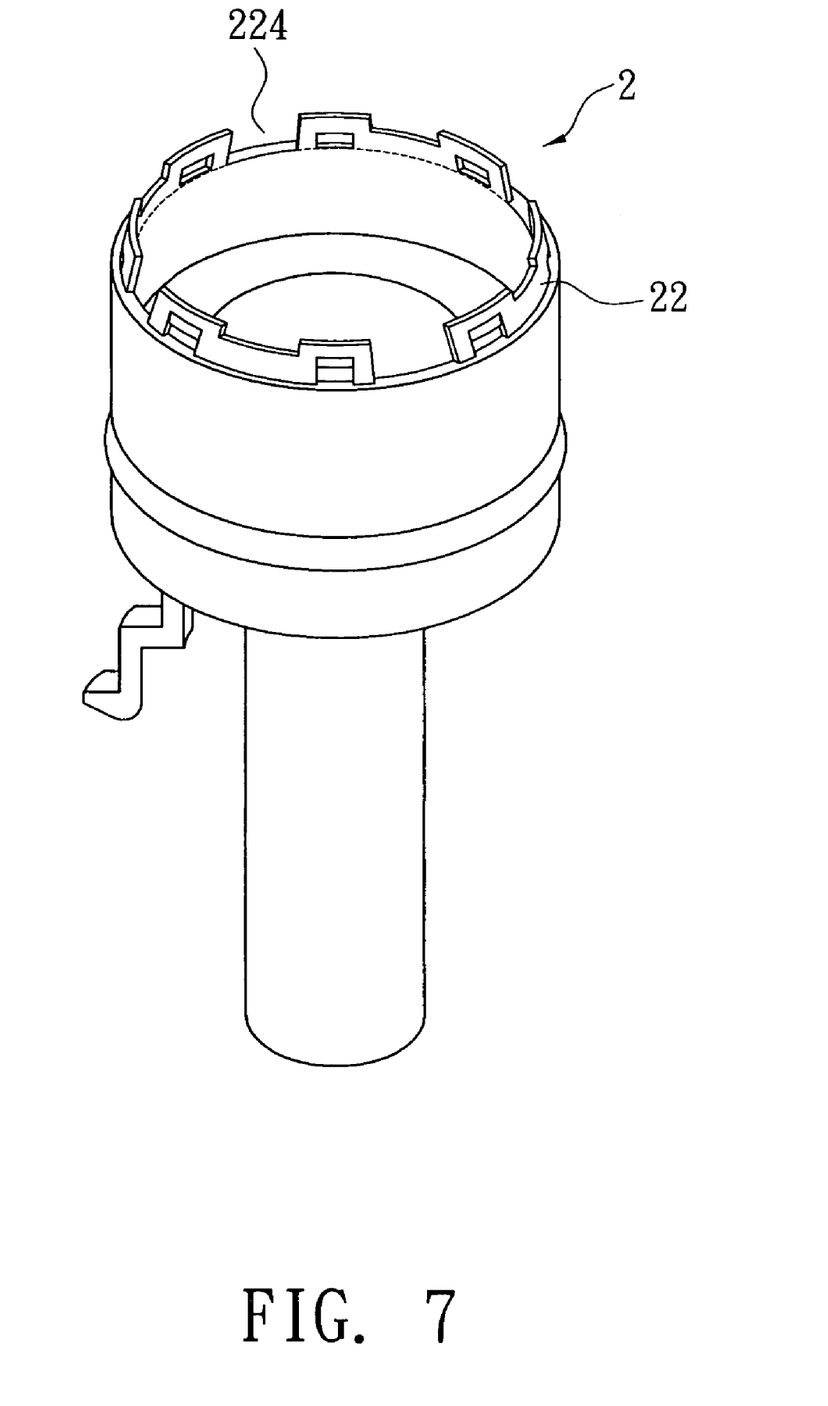
FIG. 7 is a perspective view of the needle hub with the retaining ring not bent yet according to a second embodiment of the present invention.

It is absolute that various embodiments may exist for realizing the concept of the present invention. For instance, in FIG. 7, according to a second embodiment of the present invention, the combining ring 22 of the needle hub 2 is composed of four separated pieces.

Although some particular embodiments of the invention have been described in details for purposes of illustration, it will be understood by one of ordinary skill in the art that numerous variations will be possible to the disclosed embodiments without going outside the scope of the invention as disclosed in the claims.

What is claimed is:

1. An assembly of plunger and needle hub for a safety syringe needle device comprising:

a syringe barrel, which is shaped as a tube and has an interior periphery thereof shaped as a straight tube wherein two opposite ends of the syringe barrel are respectively defined as a front end and a rear end;

a needle hub, which is inserted into the syringe barrel and comprises a retaining ring, which is sleeved by a packing ring at the external edge thereof, an accommodating room formed at one end thereof and an axially tapered combining ring, wherein a crease is formed between the interior periphery of the combining ring and the retaining ring, the crease and a plurality of through holes defined by the combining ring and adjacent to the crease provides flexibility to the combining ring, the combining ring can be bent inward to the accommodating room, and the needle hub further comprises a nozzle, which is jutting out from the syringe barrel and for being mounted by a needle; and a plunger, which comprises a plug for being fitly received by the syringe barrel, wherein the plug further has a packing ring sleeved around the edge thereof and the front end of the plug can be coupled with the combining ring of the needle hub, wherein a plurality of teeth are arranged at the upper edge of the combining ring of the needle hub and above of the plurality of through holes.

2. The assembly of plunger and needle hub as claimed in claim 1, wherein a combining portion is jutting out from the front end of the plug, wherein an annular protrusion is situated at the front end of the combining portion, which has a sectional diameter smaller than the maximum diameter of the interior periphery of the combining ring of the needle hub, and an acute-angled annular recess is formed at the combining portion adjacent to the annular protrusion for receiving and engaging the combining ring of the needle hub.

3. The assembly of plunger and needle hub as claimed in claim 1, wherein a retaining portion is provided at the interior periphery at the rear end of the syringe barrel, which is substantially composed of a plurality of inward-bent hooks that are axially extending from the syringe barrel and radially protruding for retaining the needle hub, and a peripherally enlarged annular segment is extended from the rear end of the syringe barrel, wherein the annular segment and the outer side of the inward-bent hooks are separated with an interval.

4. The assembly of plunger and needle hub as claimed in claim 1, wherein the combining ring of the needle hub is composed of a plurality of pieces.

* * * * *